US00RE38687E

(19) United States
(12) Reissued Patent
Sogabe et al.

(10) Patent Number: US RE38,687 E
(45) Date of Reissued Patent: Jan. 11, 2005

(54) CREATINE AMIDINOHYDROLASE, PRODUCTION THEREOF AND USE THEREOF

(75) Inventors: Atsushi Sogabe, Otsu (JP); Takashi Hattori, Tsuruga (JP); Yoshiaki Nishiya, Osaka (JP); Yoshihisa Kawamura, Iwakuni (JP)

(73) Assignee: Toyo Boseki Kabushiki Kaisha, Osaka (JP)

(21) Appl. No.: 09/940,941

(22) Filed: Aug. 28, 2001

Related U.S. Patent Documents

Reissue of:
(64) Patent No.: 6,080,553
Issued: Jun. 27, 2000
Appl. No.: 08/799,897
Filed: Feb. 13, 1997

(30) Foreign Application Priority Data

Feb. 13, 1996 (JP) ..... 8-025435

(51) Int. Cl.[7] ..... C12Q 1/34; C12N 9/78; C12N 1/21; C12N 15/52; C07H 21/04

(52) U.S. Cl. ..... 435/18; 435/227; 435/192; 435/252.3; 435/252.33; 435/320.1; 536/23.2

(58) Field of Search ..... 435/18, 227, 192, 435/252.3, 252.33, 320.1; 536/23.2

(56) References Cited

U.S. PATENT DOCUMENTS

| | | | |
|---|---|---|---|
| 3,806,420 | A | 4/1974 | Holz et al. |
| 3,907,644 | A | 9/1975 | Mollering et al. |
| 4,420,562 | A | 12/1983 | Ikuta et al. |
| 5,451,520 | A | 9/1995 | Furukawa et al. |

FOREIGN PATENT DOCUMENTS

| | | |
|---|---|---|
| JP | 62 091182 | 4/1987 |
| JP | 07 265074 | 10/1995 |
| JP | 07-274961 A | 10/1995 |
| JP | 10-257890 A | 9/1998 |

OTHER PUBLICATIONS

Matsuda et al., "Purification and Characterization of Creatine Amidinohydrolase of Alcaligenes Origin," *Chem. Pharm. Bull., 34*(5), 2155–2160 (1986).

Roche Molecular Biochemicals, "Creatinase, *Pseudomonas* species, recombinant," 48–51 (1999/2000).

Toyobo Co., Ltd. Catalog, "Creatine Amindinohydrolase from *Pseudomonas* sp.," TOYOBO ENZYMES (Diagnostic Reagent Grade) (1991).

Toyobo Co., Ltd. Catalog, "Creatine Amindinohydrolase from *Actinobacillus* sp.," TOYOBO ENZYMES (Diagnostic Reagent Grade), 75–78 (2000).

Yoshimoto et al., "Creatine Amidinohydrolase of *Pseudomonas putida*: Crystallization and Some Properties," *Arch. Biochem. Biophys., 177*, 508–515 (1976).

Horikoshi, "Production of Alkaline Enzymes by Alkalophilic Microorganisms," Agr. Biol. Chem., *36*(2), 285–293 (1972).

Suzuki et al., "Purification and Properties of Extracellular α–Glucosidase of a Thermophile, *Bacillus thermoglucosidius* KP 1006," Biochimica et Biophysica Acta, *445*, 386–397 (1976).

Yamada et al., "Glycerol Dehydrogenase from *Cellulomonas* sp. NT3060: Purification and Characterization," Agric. Biol. Chem., *46*(9), 2333–2339 (1982).

Yamasaki et al., "Purification and Properties of α–Glucosidase from *Penicillium purpurogenum*," Agr. Biol. Chem., *40*(4), 669–676 (1976).

Chiba et al., "Purification and Some Properties of *Saccharomyces logos* α–Glucosidase," Agr. Biol. Chem., *37*(8), 1823–1829 (1973).

Chiba et al., "Comparative Biochemical Studies on α–Glucosidases Part II. Substrate Specificity of an α–Glucosidase of *Schizosaccharomyces pombe*," Agr. Biol. Chem., *29*(6), 540–547 (1965).

Kawai et al., "Studies on Transglycosidation to Vitamin $B_6$ by Microorganisms Part V. Enzymatic Properties of Pyridoxine Glucoside–synthesizing Enzyme (α–Glucosidase) of *Micrococcus* sp. No. 431," Agr. Biol. Chem., *35*(11), 1660–1667 (1971).

Itaya et al., "Studies on Yeast Uricase Part I. Purification and Some Enzymatic Properties of Yeast Uricase," Agr. Biol. Chem., *31*(11), 1256–1264 (1967).

Tanaka et al., "Purification and Properties of β–Galactosidase from *Aspergillus oryzae*," J. Biochem., *77*, 241–247 (1975).

Yamasaki et al., "Purification and Properties of α–Glucosidase from *Bacillus cereus*," Agr. Biol. Chem., *38*(2), 443–454 (1974).

Kitahata et al., "Purification and Some Properties of *Candida tropicalis* α–Glucosidase," Kagaku to Kogyo, *62*(9), 363–367 (1988).

Fukumoto et al., "Studies on Lipase IV. Purification and Properites of a Lipase Secreted by *Rhizopus Delemar*," J. Gen. Appl. Microbiol., *10*(3), 257–265 (1964).

(List continued on next page.)

*Primary Examiner*—Elizabeth Slobodyansky
(74) *Attorney, Agent, or Firm*—Leydig, Voit & Mayer, Ltd.

(57) ABSTRACT

A creatine amidinohydrolase having the following physicochemical properties:

Action: catalyzing the following reaction; creatine+$H_2O$→sarcosine+urea

Optimum temperature: about 40–50° C.

Optimum pH: pH about 8.0–9.0

Heat stability: not more than about 50° C. (pH 7.5, 30 min)

Km value for creatine in a coupling assay using a sarcosine oxidase and a peroxidase: about 3.5–10.0 mM Molecule weight: about 43,000 (SDS-PAGE)

Isoelectric point: about [3.5] *4.5,* a method for producing said enzyme, comprising culture of microorganism producing said enzyme, a method for the determination of creatine or creatinine in a sample using said enzyme, and a reagent therefor.

37 Claims, 2 Drawing Sheets

OTHER PUBLICATIONS

Uwajima et al., Purification and Properties of Cholesterol Esterase from *Pseudomonas fluorescens*, Agr. Biol. Chem., *40*(10), 1957–1964 (1976).

Nakanishi et al., "Purification and Some Properties of an Alkalophilic Proteinase of a *Streptomyces* Species," Agr. Biol. Chem., *38*(1), 37–44 (1974).

Suzuki et al., "Purification and Characterization of *Bacillus coagulans* Oligo–1,6–Glucosidase," Eur. J. Biochem., *158*, 77–83 (1986).

Makino et al., Purification and Characterization of a New Glucose Dehydrogenase from Vegetative Cells of *Bacillus megaterium*, Journal of Fermentation and Bioengineering, *67*(6), 374–379 (1989).

Kato et al., "Alcohol Oxidases of *Kloeckera* sp. and *Hansenula polymorpha*," Eur. J. Biochem., *64*, 341–350 (1976).

Huang et al., "Purification and Characterization of Thermostable Glycerol Kinase from *Thermus flavus*," Journal of Fermentation and Bioengineering, *83*(4), 328–332 (1997).

Sugiura et al., "Purification and Properties of a *Chromobacterium* Lipase with a High Molecular Weight," Agr. Biol. Chem., *38*(5), 947–952 (1974).

Tsuru et al., "Purification and Characterization of L–Pyrrolidonecarboxylate Peptidase from *Bacillus amyloliquefaciens*," J. Biochem., *84*, 467–476 (1978).

Geiger et al., "Reversible Thermal Inactivation of the Quinoprotein Glucose Dehydrogenase from *Acinetobacter calcoaceticus*," Biochem. J., *261*, 415–421 (1989).

CREATINE AMIDINOHYDROLASE, PRODUCTION THEREOF AND USE THEREOF

Matter enclosed in heavy brackets [ ] appears in the original patent but forms no part of this reissue specification; matter printed in italics indicates the additions made by reissue.

*CROSS-REFERENCE TO RELATED APPLICATIONS*

*More than one reissue application has been filed for the reissue of U.S. Pat. No. 6,080,553. The reissue applications are Application No. 09/940,941 (the present application) and Application No. 10/807,228, which are divisional reissues of U.S. Pat. No. 6,080,553.*

FIELD OF THE INVENTION

The present invention relates to a novel creatine amidinohydrolase, specifically, a novel creatine amidinohydrolase having a very low Km value for creatine, and a method for producing said enzyme. The present invention also relates to a method for the determination of creatine or creatinine in a sample by the use of said enzyme, and a reagent therefor.

BACKGROUND OF THE INVENTION

A creatine and a creatinine are found in blood and urine. A quick and accurate determination of their amounts is very important in making diagnosis of the diseases such as uremia, chronic neophritis, acute neophritis, giantism, tonic muscular dystrophy and the like. For making diagnosis of these diseases, creatine and creatinine in blood, as well as urine are frequently determined quantitatively.

A creatine can be determined by allowing creatine amidinohydrolase and sarcosine oxidase to react on creatine in a sample and determining the amount of the generated hydrogen peroxide by a method for measuring hydrogen peroxide. A creatinine can be determined by allowing creatinine amidohydrolase, creatine amidinohydrolase and sarcosine oxidase to react on creatinine in a sample and determining the generated hydrogen peroxide by a method for measuring hydrogen peroxide.

The creatinine amidohydrolase, creatine amidinohydrolase and sarcosine oxidase are widely found in the world of microorganisms, have been industrially produced and used as reagents for clinical tests.

Yet, the creatine amidinohydrolase produced from various known cell lines show lower heat stability and greater Km value for creatine. For example, an enzyme derived from the bacteria belonging to the genus Bacillus (U.S. Pat. No. 4,420,562) is thermally stable only at a temperature not more than 40° C. An enzyme derived from Pseudomonas putida has a smaller apparent Km value for creatine of 1.33 mM [Archives Biochemistry and Biophysics 177, 508–515 (1976)], though the method for determining the activity is different and the Km value for creatine determined by a coupling assay using sarcosine oxidase and peroxidase widely used as reagents for clinical tests, has been unknown. The enzymes derived from the bacteria belonging to the genus Corynebacterium, Micrococcus, Actinobacillus or Bacillus (Japanese Patent Examined Publication No. 76915/1991) is thermally stable at a temperature not more than 50° C., whereas Km value for creatine is as great as about 20 mM, and these enzymes are not suitable for use as reagents for clinical tests.

In an attempt to resolve such problems, the present inventors previously found that the bacteria belonging to the genus, Alcaligenes produced a creatine amidinohydrolase which was superior in heat stability and had a relatively smaller Km value (Km value: ca. 15.2) for creatine (Japanese Patent Unexamined Publication No. 63363/1994). Furthermore, they have established a technique for isolating a creatine amidinohydrolase gene having a relatively small Km value for creatine from said bacterial cell line and producing said enzyme in a large amount using Gram negative bacteria as a host (Japanese Patent Application No. 117283/1995).

Moreover, a creatine amidinohydrolase stable in a high pH range and having a small Km value has been reported to be derived from the same genus Alcaligenes cell lines (U.S. Pat. No. 5,451,520).

Yet, these creatine amidinohydrolases still have greater Km values as enzymes to be used as routine reagents for clinical tests, and a creatine amidinohydrolase having smaller Km value has been desired.

SUMMARY OF THE INVENTION

It is therefore an object of the present invention to produce a novel creatine amidinohydrolase having a small Km value for creatine to the extent sufficient for use as a general reagent for clinical tests, preferably not more than about 15.0, and provide a means for determining creatine or creatinine in a sample using said enzyme.

The present invention is based on the successful provision of a creatine amidinohydrolase gene which expresses a novel creatine amidinohydrolase having a small Km value for creatine, by introducing a mutation, by genetic engineering and protein engineering, into a creatine and amidinohydrolase gene derived from conventionally known bacteria belonging to the genus Alcaligenes, which is a known creatine amidinohydrolase having a rather small Km value. The creatine amidinohydrolase of the present invention can be produced in large amounts by culturing a microorganism capable of expressing said gene in a nutrient medium.

The novel creatine amidinohydrolase of the present invention has a very small Km value for creatine as compared to conventionally known enzymes, and shows superior reactivity to creatine contained in a trace amount in a sample. Thus, it is useful as a reagent for determining creatine or creatinine with high sensitivity and high precision.

Accordingly, the present invention provides a novel creatine amidinohydrolase having the following physicochemical properties.

Action: catalyzing the following reaction:

creatine+$H_2O$→sarcosine+urea

Optimum temperature: ca. 40–50° C.

Optimum pH: ca. 8.0–9.0

Heat stability: stable at not more than 50° C. (pH 7.5, 30 min)

Km value relative to creatine in a coupling assay using a sarcosine oxidase and a peroxidase: ca. 3.5–10.0 mM Molecular weight: ca. 43,000 (SDS-PAGE)

Isoelectric point: ca. [3.5] *4.5*

The present invention also provides a method for producing said creatine amidinohydrolase, comprising culturing a microorganism capable of producing a novel creatine amidinohydrolase having the following physicochemical properties, in a nutrient medium, and harvesting said creatine amidinohydrolase from the culture.

Action: catalyzing the following reaction:

creatine+$H_2O$→sarcosine+urea

Optimum temperature: ca. 40–50° C.

Optimum pH: ca. 8.0–9.0

Heat stability: stable at not more than about 50° C. (pH 7.5, 30 min)

Km value relative to creatine in a coupling assay using a sarcosine oxidase and a peroxidase: ca. 3.5–10.0 mM Molecular weight: ca. 43,000 (SDS-PAGE)

Isoelectric point: ca. [3.5] *4.5*

The present invention further provides a reagent for determining creatine in a sample, comprising the above-said creatine amidinohydrolase, sarcosine oxidase and a composition for detection of hydrogen peroxide, and a method for determining creatine in a sample by the use of said reagent.

The present invention further provides a reagent for determining creatinine in a sample, comprising a creatinine amidohydrolase, the above-mentioned creatine amidinohydrolase, sarcosine oxidase and a composition for detection of hydrogen peroxide, and a method for determining creatinine in a sample by the use of said reagent.

DETAILED DESCRIPTION OF THE INVENTION

Figure 1:
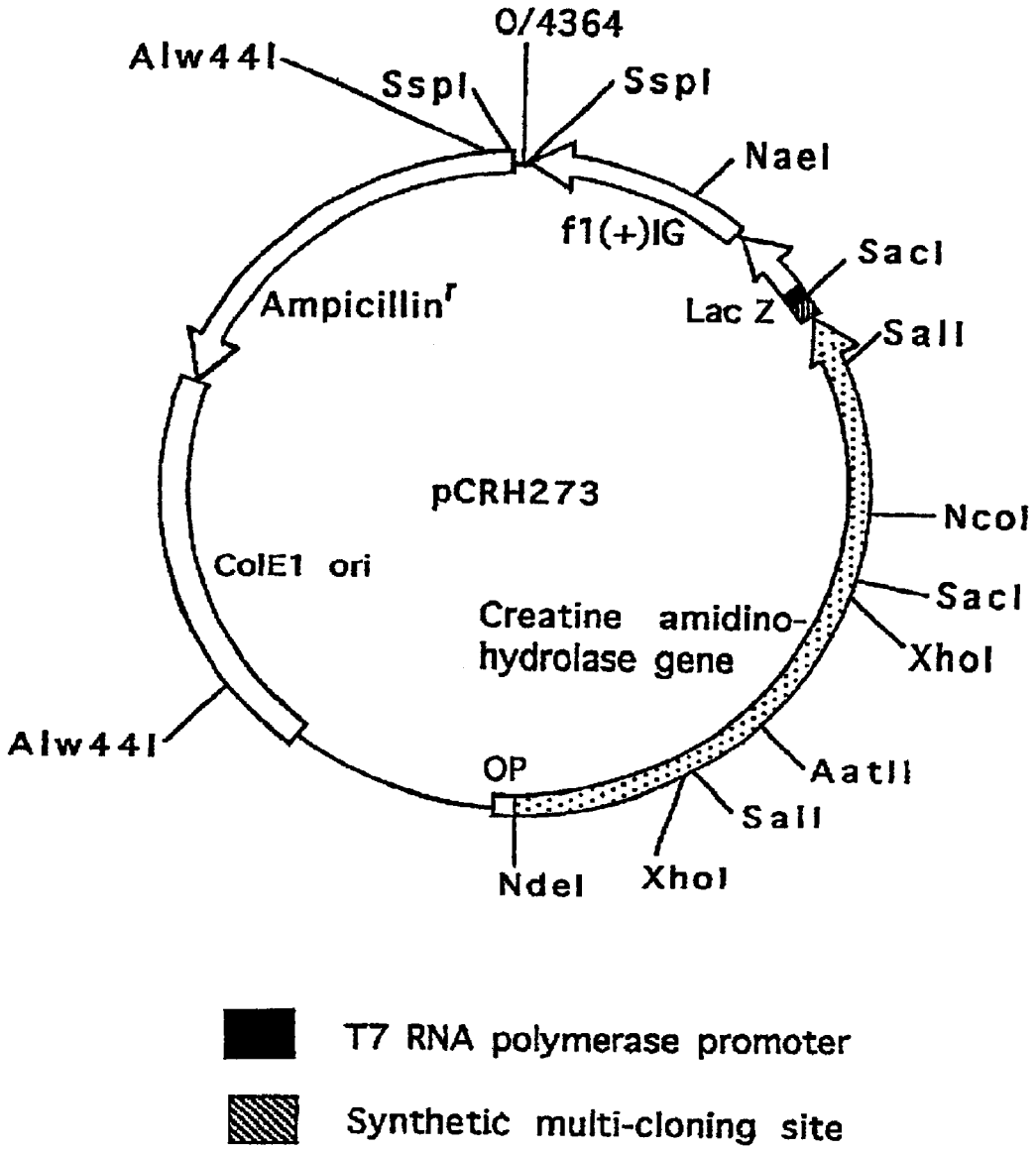
FIG. 1 shows a physical map of recombinant plasmid pCRH273.

One embodiment of the present invention is a novel creatine amidinohydrolase having the following physicochemical properties;

Action: catalyzing the following reaction: creatine+$H_2O$→sarcosine+urea

Optimum temperature: ca. 40–50° C.

Optimum pH: ca. 8.0–9.0

Heat stability: stable at not more than about 50° C. (pH 7.5, 30 min)

Km value relative to creatine in a coupling assay using a sarcosine oxidase and a peroxidase: ca. 4.5±1.0 mM Molecular weight: ca. 43,000 (SDS-PAGE)

Isoelectric point: ca. [3.5] *4.5*

Another embodiment of the present invention is a novel creatine amidinohydrolase having the following physicochemical properties.

Action: catalyzing the following reaction: creatine+$H_2O$→sarcosine+urea

Optimum temperature: ca. 40–50° C.

Optimum pH: ca. 8.0–9.0

Heat stability: stable at not more than about 50° C. (pH 7.5, 30 min)

Km value relative to creatine in a coupling assay using a sarcosine oxidase and a peroxidase: ca. 6.5±1.0 mM Molecular weight: ca. 43,000 (SDS-PAGE)

Isoelectric point: ca. [3.5] *4.5*

A still another embodiment of the present invention is a novel creatine amidinohydrolase having the following physicochemical properties.

Action: catalyzing the following reaction: creatine+$H_2O$→sarcosine+urea

Optimum temperature: ca. 40–50° C.

Optimum pH: ca. 8.0–9.0

Heat stability: stable at not more than about 50° C. (pH 7.5, 30 min)

Km value relative to creatine in a coupling assay using a sarcosine oxidase and a peroxidase: ca. 9.0±1.0 mM Molecular weight: ca. 43,000 (SDS-PAGE)

Isoelectric point: ca. [3.5] *4.5*

One method for producing the creatine amidinohydrolase of the present invention comprises mutation of a gene encoding a wild creatine amidinohydrolase by genetic engineering and protein engineering method, generating a mutant DNA encoding a novel creatine amidinohydrolase having a smaller Km value for creatine than the wild creatine amidinohydrolase, expressing said DNA in a suitable host and harvesting the creatine amidinohydrolase thus produced.

While the gene encoding a wild creatine amidinohydrolase which is to be mutated is not particularly limited, in one embodiment of the present invention, it is the creatine amidinohydrolase gene depicted in the Sequence Listing•SEQ ID:No.2, which is derived from Alcaligenes•faecalis TE3581 (FERM P-14237).

In another embodiment of the present invention, a novel creatine amidinohydrolase having a smaller Km value for creatine than a wild creatine amidinohydrolase is produced by mutating the gene encoding the amino acid sequence depicted in the Sequence Listing•SEQ ID:No.1.

A wild creatine amidinohydrolase gene can be mutated by any known method. For example, a wild creatine amidinohydrolase DNA or a microorganism cells having said gene is brought into contact with a mutagenic agent, or ultraviolet irradiation is applied, or a protein engineering method is used such as PCR and site-directed mutagenesis. Alternatively, an Escherichia coli susceptible to gene mutation at high frequency due to defective gene repair mechanism may be transformed with a wild creatine amidinohydrolase gene DNA for mutation in vivo.

For example, Escherichia coli is transformed with the mutant creatine amidinohydrolase gene obtained above and plated on a creatine amidinohydrolase activity detection agar medium [J. Ferment. Bioeng., Vol. 76 No. 2 77–81(1993)], and the colonies showing clear color development are selected. The selected colonies are incubated to a nutritive medium (e.g., LB medium and 2×YT medium) and cultured overnight at 37° C. The cells are disrupted and a crude enzyme solution is extracted.

The method for disrupting the cells may be any known method, such as physical rupture (e.g., ultrasonication and glass bead rupture), as well as by the use of a lysozyme. This crude enzyme solution is used to determine the creatine amidinohydrolase activity of two kinds of activity determination reaction solutions having different substrate concentrations. Comparison of the activity ratios of the two with that obtain using a wild creatine amidinohydrolase leads to the screening of the creatine amidinohydrolase having smaller Km value.

The method for obtaining the purified creatine amidinohydrolase from the cell line selected as above may be any known method, such as the following.

After the cells obtained by culturing in a nutrient medium are recovered, they are ruptured by an enzymatic or physical method and extracted to give a crude enzyme solution. A creatine amidinohydrolase fraction is recovered from the obtained crude enzyme solution by ammonium sulfate precipitation. The enzyme solution is subjected to desalting by Sephadex G-25 (Pharmacia BioTech) gel filtration and the like.

After this operation, the resulting enzyme solution is separated and purified by octyl Sepharose CL-6B (Pharmacia Biotech) column chromatography to give a standard purified enzyme product. This product is purified to the degree that it shows almost a single band by SDS-PAGE.

The microorganisms to be used in the present invention to produce the novel creatine amidinohydrolase is exemplified by Escherichia coli JM109 (pCRH273M1) (FERM BP-5374), Escherichia coli JM109 (pCRH273M2) (FERM BP-5375), Escherichia coli JM109 (pCRH273M3) (FERM BP-5376) and the like.

The method for culturing these microorganisms and recovering the creatine amidinohydrolase of the present invention from the cultures thereof are not particularly limited, and conventional methods can be applied.

The novel creatine amidinohydrolase obtained by the above-mentioned production method of the present invention has the following physicochemical properties.

Action: catalyzing the following reaction:

creatine+$H_2O$→sarcosine+urea

Optimum temperature: ca. 40–50° C.

Optimum pH: ca. 8.0–9.0

Heat stability: stable at not more than about 50° C. (pH 7.5, 30 min)

Km value relative to creatine in a coupling assay using a sarcosine oxidase and a peroxidase: ca. 3.5–10.0 mM Molecular weight: ca. 43,000 (SDS-PAGE)

Isoelectric point: ca. [3.5] *4.5*

The Km value in the present invention is the value relative to creatine in a coupling assay using a sarcosine oxidase and a peroxidase. While the conventional enzyme derived from Pseudomonas putida has a small apparent Km value for creatine of 1.33 mM [Archives Biochemistry and Biophysics 177, 508–515 (1976)], the activity is determined by measuring the residual creatine in the reaction mixture with α-naphthol and diacetyl, and the Km value for creatine by a coupling assay using a sarcosine oxidase and a peroxidase, which are widely used as reagents for clinical tests, has been unknown.

The creatine amidinohydrolase of the present invention can be used for the determination of creatine upon combination with a sarcosine oxidase and a composition for detection of hydrogen peroxide. Moreover, when creatinine amidohydrolase is concurrently used, creatinine can be determined as well.

The determination method of the present invention utilizes the following reactions.

Reaction 1:

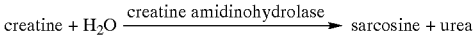

Reaction 2:

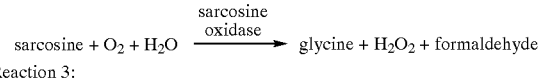

Reaction 3:

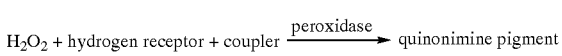

When creatinine is determined, the following reaction is further utilized.

Reaction 4:

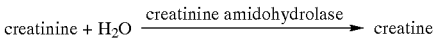

The quinonimine pigment produced is generally subjected to the determination of absorbance at 500–650 nm wavelength. The method for determining creatine is an end method on a rate method, though the end method is generally used.

The inventive creatine amidinohydrolase having smaller Km value can reduce the amount of the enzyme to be used in the test reagent for creatine or creatinine determination to about ⅓–¼ as compared to the necessary amount of conventional enzymes, and achieves good reactivity in the latter half of the reaction.

The reagent for determining creatine in a sample of the present invention contains the above-mentioned creatine amidinohydrolase, sarcosine oxidase, and a composition for detecting hydrogen peroxide.

The reagent for determining creatinine in a sample of the present invention contains a creatinine amidohydrolase, the above-mentioned creatinine amidohydrolase, sarcosine oxidase, and a composition for detecting hydrogen peroxide.

The sarcosine oxidase to be used for detecting the creatine or creatinine of the present invention can be obtained from the microorganisms originated from the genera Arthrobacter, Corynebacterium, Alcaligenes, Pseudomonas, Micrococcus, Bacillus and the like, and some of them are commercially available.

The creatinine amidohydrolase can be obtained from the microorganisms originated from the genera Pseudomonas, Flavobacterium, Alcaligenes, Penicillium and the like, and some of them are commercially available.

The composition for the detection of hydrogen peroxide contains an enzyme having a peroxide activity, chromophore and a buffer. The enzyme having a peroxidase activity is exemplified by peroxidase, haloperoxidase, bromoperoxidase lactoperoxidase, myeloperoxidase and the like. The chromophore comprises a hydrogen receptor and a coupler. The hydrogen receptor may be any as long as it receives hydrogen in the reaction with hydrogen peroxide, peroxidase and a coupler, which is specifically exemplified by 4-aminoantipyrine, 3-methyl-2-benzothiazoline-hydrozine derivative and the like. Examples of the coupler include aniline derivatives such as aniline and N-ethyl-N-(2-hydroxy-3-sulfopropyl)-m-toluidine (TOOS), phenol derivatives such as phenol and p-chlorophenol, and the like.

The reagent for the determination of creatine of the present invention contains each ingredient in a preferable proportion of creatine amidinohydrolase ca. 5–300 U/ml, sarcosine oxidase ca. 1–100 U/ml, peroxidase ca. 0.01–50 U/ml, hydrogen donor ca. 0.1–10 mM, and a coupler ca. 0.1–50 mM.

The reagent for the determination of creatinine of the present invention contains each ingredient in a preferable proportion of creatinine amidohydrolase ca. 10–300 U/ml, creatine amidinohydrolase ca. 10–300 U/ml, sarcosine oxidase ca. 1–100 U/ml, peroxidase ca. 0.01–50 U/ml, hydrogen donor ca. 0.1–10 mM, and a coupler ca. 0.1–50 mM.

The reagent for the determination of creatine or creatinine of the present invention is generally used with a buffer having a pH of about 6–8. Examples of the buffer include phosphate buffer, Good buffer, Tris buffer and the like.

Where necessary, ascorbate oxidase or catalase may be added to the reagent of the present invention. Other compounds may be also added to the reagent of the present invention for smooth enzyme reaction and color development. Such compounds are, for example, stabilizers, surfactants, excipients and the like.

EXAMPLES

The present invention is described in detail by way of the following Examples.

In the Examples, the activity of creatine amidinohydrolase was determined as follows. The enzyme activity in the present invention is defined to be the enzyme amount capable of producing 1 μmole of sarcosine per min under the following conditions being one unit (U).

| Reaction mixture composition | |
|---|---|
| 0.3 H | HEPES pH 7.6 |
| 0.005% | 4-aminoantipyrine |
| 0.015% | phenol |
| 1.8% | creatine |
| 6 U/ml | sarcosine cridase |
| 6 U/ml | peroxidase |

The above-mentioned reaction mixture (3 ml) is taken with a cuvette (d=1 cm) and preliminary heated to 37° C. for about 3 minutes. An enzyme solution (0.1 ml) is added, and the mixture is gently admixed. Using water as a control, changes in absorbance at 500 nm are recorded for 5 minutes using a spectrophotometer controlled to 37° C. Based on the linear portion of 2–5 minutes thereof, changes in absorbance per minute are determined (ΔOD test).

The blank test is performed in the same manner as above except that a solution (0.1 ml, 50 mM potassium phosphate buffer, pH 7.5) for diluting the enzyme is used instead of the enzyme solution and changes in absorbance per minute are determined (ΔOD blank).

The enzyme amount is calculated by inserting each measure into the following formula.

$$\text{U/ml} = \frac{\Delta\text{OD}/\text{min}(\Delta\text{OD test} - \Delta\text{OD blank}) \times 3.1 \times \text{dilutions fold}}{13.3 \times 1/2 \times 1.0 \times 0.1}$$

wherein each constant denotes the following:

13.3: millimolar absorbance coefficient ($cm^2/\mu M$) under the above measurement conditions of quinonimine pigment ½: coefficient indicating that the quinonimine pigment formed from one molecule of hydrogen peroxide generated in the enzyme reaction is ½ molecule 1.0: light path length (cm)

0.1: amount of enzyme added (ml)

Reference Example 1

Isolation of chromosomal DNA

The chromosomal DNA of Alcaligenes•faecalis TE3581 was isolated by the following method.

The cells (FERM P-14237) were shake-cultured overnight at 30° C. in a nutrient broth (150 ml) and the cells were collected by centrifugation (8000 rpm, 10 min). The cells were suspended in a solution (5 ml) containing 10% sucrose, 50 mM Tris-HCl (pH 8.0) and 50 mM EDTA, and a lysozyme solution (1 ml, 10 mg/ml) was added. The mixture was incubated at 37° C. for 15 min. Then, 10% SDS solution (1 ml) was added. An equivalent amount (1 ml) of a choroform•phenol solution (1:1) was added to this mixture. The mixture was stirred and separated into an aqueous layer and a solvent layer by centrifugation at 10,000 rpm for 3 min. The aqueous layer was separated, and onto this aqueous layer was gently layered a 2-fold amount of ethanol. The content was slowly stirred with a glass rod to allow the DNA to wind around the rod.

This DNA was dissolved in 10 mM Tris-HCl solution (pH 8.0, hereinafter abbreviated as TE) containing 1 mM EDTA. This solution was treated with an equivalent amount of chloroform•phenol solution. The aqueous layer was separated by centrifugation, and a 2-fold amount of ethanol was added. The DNA was separated again by the method described above and dissolved in 2 ml of TE.

Reference Example 2

Preparation of DNA fragment containing a gene encoding creatinine amidinohydrolase and recombinant vector containing said DNA fragment The DNA (20 μg) obtained in Reference Example 1 was partially cleaved with restriction enzymes Sau3AI (Toyo Boseki Kabushiki Kaisha) and 2–10 kbp fragments were recovered by sucrose density gradient centrifugation. Meanwhile, pBluescript KS(+) cleaved with restriction enzyme BamHI (Toyo Boseki Kabushiki Kaisha) was dephosphorylated with bacterial alkaline phosphatase (Toyo Boseki Kabushiki Kaisha). Then, the both DNAs were treated with T4DNA ligase (1 unit, Toyo Boseki Kabushiki Kaisha) at 16° C. for 12 hr to ligate the DNA. Escherichia coli JM109 competent cell (Toyo Boseki Kabushiki Kaisha) was transformed with the ligated DNA and plated onto a creatine amidinohydrolase activity detection agar medium [0.5% yeast extract, 0.2% meat extract, 0.5% polypeptone, 0.1% NaCl, 0.1% $KH_2PO_4$, 0.05% $MgSO_4/7H_2O$, 1.15% creatine, 10 U/ml sarcosine oxidase (Toyo Boseki Kabushiki Kaisha), 0.5 U/ml peroxidase (Toyo Boseki Kabushiki Kaisha), 0.01% o-dianisidine, 50 μg/ml ampicillin and 1.5% agar]. The activity of creatine amidinohydrolase was detected using, as the indices, the colonies grown in the above-mentioned medium and stained in brown. The colonies (ca. $1\times10^5$) of the transformant were obtained per DNA 1 μg used.

About 12,000 colonies were screened, and 6 colonies were found stained in brown. These strains were obtained in LB liquid medium (1% polypeptone, 0.5% yeast extract, 0.5% NaCl, 50 μg/ml ampicillin) and creatine amidinohydrolase activity was determined, as a result of which creatine amidinohydrolase activity was detected in every strain. The plasmid of the strain which showed the highest creatine amidinohydrolase activity contained ca. 5 kbp insert DNA fragment, and this plasmid was named pCRH17.

Then, the insert DNA of pCRH17 was cleaved with restriction enzymes EcoRV (Toyo Boseki Kabushiki Kaisha) and PstI (Toyo Boseki Kabushiki Kaisha), and ligated to pBluescript KS(+) cleaved with said restriction enzymes to prepare pCRH173.

Example 1

Preparation of recombinant plasmid pCRH273 by mutating creatine amidinohydrolase gene The region of from β-galactosidase structural gene derived from the vector to the upstream region of the creatine amidinohydrolase structural gene of the insert DNA was deleted from the recombinant plasmid pCRH173 of Reference Example 2, using the synthetic DNA depicted in SEQ ID:No.3 and a commercially available mutation introduction kit (Transformer™; Clonetech) to prepare recombinant plasmid pCRH173M. The detailed method for introducing the mutation was given in the protocol attached to the kit.

The pCRH173M was cleaved with restriction enzyme EcoRI (Toyo Boseki Kabushiki Katsha) and self-ligated to prepare pCRH273 (FIG. 1).

Example 2

Selection of candidate cell lines producing the objective mutant creatine amidinohydrolase A commercially available Escherichia coli competent cell (E. coli XLI-Red; Clonetech) was transformed with the pCRH273 prepared in Example 1, and the entire amount thereof was inoculated to 3 ml of LB liquid medium (1% polypeptone, 0.5% yeast extract, 1.0% NaCl) containing ampicillin (50 μg/ml; Nakarai Tesque), which was followed by shake culture overnight at 37° C. A plasmid was recovered from the entire amount of this culture by a conventional method. The commercially available Escherichia coli competent cell (E. coli JM109, Toyo Boseki Kabushiki Kaisha) was transformed again with this plasmid and plated onto a creatine amidinohydrolase activity detected agar medium, which was then incubated overnight at 37° C. The cell lines which showed a strong expression of the creatine amidinohydrolase activity, i.e., the strains which showed a deep color development, were selected from the mutant creatine amidinohydrolase library thus obtained.

Example 3

Screening of creatine amidinohydrolase-producing cell line having a record Km value The candidate cell lines selected in Example 2 were inoculated to 3 ml of TB medium (1.2% polypeptone, 2.4% yeast extract, 0.4% glycerol, 0.0231% $KH_2PO_4$, 0.1254% $K_2HPO_4$) containing ampicillin (200 μg/ml) and shake-cultured overnight at 37° C. The cells were recovered from 1 ml of culture by centrifugation, and a crude enzyme solution was prepared therefrom by rupture with glass beads. Using the crude enzyme solution thus obtained and following the above-mentioned activity determination method, creatine amidinohydrolase was determined. Meanwhile, using an activity determination reagent having a 1/10 substrate concentration, the creatine amidinohydrolase activity was determined in the same manner. The cell line wherein the ration of two kinds of the activity measures (activity with 1/10 substrate concentration+activity obtained by conventional manner) increased beyond that of a wild creatine amidinohydrolase was selected as a mutant having a reduced Km value.

About 20,00 cell lines were screened by the above method, and three mutant cell lines having a smaller Km value for creatine were obtained, and the respective recombinant plasmids thereof were named pCRH273M1 (FERM BP-5374), pCRH273M2 (FERM BP-5375) and pCRH273M3 (FERM BP-5376).

Example 4

Preparation of creatine amidinohydrolase from Escherichia coli JM109 (pCRH273M1)

TB medium (6 L) was disposed to 10 L jar fermentors, and subjected to autoclaving at 121° C. for 15 min. After allowing them to cool, 50 mg/ml ampicillin (Nakarai Tesque) and 200 mM IPTG (Nippon Seika Corp.), which had been separately sterilized by filtration were added by 6 ml each. To this medium was added 60 ml of the culture of Escherichia coli JM109 (pCRH273M1) (FERM BP-5374) after previous shake culture at 30° C. for 24 hr, which was followed by aeration culture at 37° C. for 24 hr. The activity of creatine amidinohydrolase after the completion of the culture was 8.7 U/ml.

The above-mentioned cells were collected by centrifugation, and suspended in 50 mM phosphate buffer, pH 7.0.

The cells in this suspension were ruptured with a French press and subjected to centrifugation to give a supernatant. The obtained crude enzyme solution was subjected to ammonium sulfate fractionation, desalting with Sephadex G-25 (Pharmacia Biotech) gel filtration and purified by octyl Sepharose CL-6B (Pharmacia Biotech) column chromatography to give a purified enzyme product. The standard creatine amidinohydrolase product obtained by this method showed a nearly single band by SDS-PAGE and had a specific activity then of 18.4 U/mg protein.

Table 1 shows the purification performed so far. Table 2 shows physicochemical properties of the creatine amidinohydrolase obtained by the above methods.

TABLE 1

Purification of creatine amidinohydrolase from Escherichia coli JM109 (pCRH273M1)

| Step | Total activity (U) | Specific activity (U/mg-protein) | Yield (%) |
|---|---|---|---|
| French press rupture | 52200 | | 100.0 |
| $(NH_4)_2SO_4$ precipitation-redissolution | 49746 | 8.3 | 95.3 |
| Sephadex G-25 | 46927 | 10.3 | 89.9 |
| Octyl Sepharose CL-6B | 33094 | 18.4 | 63.4 |

TABLE 2

Physicochemical properties of creatine amidinohydrolase purified from Escherichia coli JM109 (pCRH273M1)

| Item | Physicochemical properties |
|---|---|
| Action | creatine + $H_2O$ → sarcosine + urea |
| Optimal temperature | ca. 40° C.–50° C. |
| Optimal pH | ca. 8.0–9.0 |
| Thermal stability | ca. 50° C.(50 mM potassium phosphate buffer, pH 7.5, 30 min treatment) |
| pH stability | ca. 5–8 (40° C., 18 hr preservation) |
| Km value | ca. 6.5 mM (creatine) |
| Molecular weight | ca. 43,000 (SDS-PAGE) |
| Isoelectric point | ca. [3.5] *4.5* (isoelectric focusing) |

Example 5

Preparation of creatine amidinohydrolase from Escherichia coli JM109 (pCRH273M2)

TB medium (6 L) was dispersed to 10 L jar fermentors, and subjected to autoclaving at 121° C. for 15 min. After allowing them to cool, 50 mg/ml ampicillin (Nakarai Tesque) and 200 mM IPTG (Nippon Seika Corp.), which had been separately sterilized by filtration, were added by 6 ml each. To this medium was added 60 ml of the culture of Escherichia coli JM109 (pCRH273M2) (FERM BP-5375) after previous shake culture at 30° C. for 24 hr, which was followed by aeration culture at 37° C. for 24 hr. The activity or creatine amidinohydrolase after the completion of the culture was 5.6 U/ml.

The above-mentioned cells were collected by centrifugation, and suspended in 50 mM phosphate buffer, pH 7.0.

The cells in this suspension were ruptured with a French press and subjected to centrifugation to give a supernatant. The obtained crude enzyme solution was subjected to ammonium sulfate fractionation, desalting with Sephadex G-25 (Pharmacia Biotech) gel filtration and purified by octyl Sepharose CL-6B (Pharmacia Biotech) column chromatography to give a purified enzyme product. The standard creatine amidinohydrolase product obtained by this method showed a nearly single band by SDS-PAGE and had a specific activity then of 14.3 U/mg protein.

Table 3 shows the purification performed so far. Table 4 shows physicochemical properties of the creatine amidinohydrolase obtained by the above methods.

TABLE 3

Purification of creatine amidinohydrolase from Escherichia Coli JM109 (pCRH273M2)

| Step | Total Activity (U) | Specific activity (U/mg-protein) | Yield (%) |
|---|---|---|---|
| French press rupture | 33600 | | 100.0 |
| $(NH_4)_2SO_4$ precipitation-redissolution | 25636 | 7.2 | 76.3 |
| Sephadex G-25 | 24326 | 9.8 | 72.4 |
| Octyl Sepharose CL-6B | 19689 | 14.3 | 58.6 |

TABLE 4

Physicochemical properties of creatine amidinohydrolase purified from Escherichia coli JM109 (pCRH273M2)

| Item | Physicochemical properties |
|---|---|
| Action | creatine + $H_2O$ → sarcosine + urea |
| Optimal temperature | ca. 45° C.–50° C. |
| Optimal pH | ca. 8.0–9.0 |
| Thermal stability | ca. 40° C. (50 mM potassium phosphate buffer, pH 7.5, 30 min treatment) |
| pH stability | ca. 5–8 (40° C., 18 hr preservation) |
| Km value | ca. 4.5 mM (creatine) |
| Molecular weight | ca. 43,000 (SDS-PAGE) |
| Isoelectric point | ca. [3.5] *4.5* (isoelectric focusing) |

Example 6

Preparation of creatine amidinohydrolase from Escherichia coli JM109 (pCRH273M3)

TB medium (6 L) was dispensed to 10 L jar fermentors, and subjected to autoclaving at 121° C. for 15 min. After allowing them to cool, 50 mg/ml ampicillin (Nakarai Tesque) and 200 mM IPTG (Nippon Seika Corp.) which had been separately sterilized by filtration were added by 6 ml each. To this medium was added 60 ml of culture of Escherichia coli JM109 (pCRH273M3) (FERM BP-5376) after previous shake culture at 30° C. for 24 hr, which was followed by aeration culture at 37° C. for 24 hr. The activity of creatine amidinohydrolase after the completion of the culture was 8.3 U/ml.

The above-mentioned cells were collected by centrifugation, and suspended in 50 mM phosphate buffer, pH 7.0.

The cells in this suspension were ruptured with a French press and subjected to centrifugation to give a supernatant. The obtained crude enzyme solution was subjected to ammonium sulfate fractionation, desalting by Sephadex G-25 (Pharmacia Biotech) gel filtration and purified by octyl Sepharose CL-6B (Pharmacia Biotech) column chromatography to give a purified enzyme product. The standard creatine amidinohydrolase product obtained by this method showed a nearly single band by SDS-PAGE and had a specific activity then of 14.8 U/mg protein.

Table 5 shows the purification performed so far. Table 6 shows physicochemical properties of the creatine amidinohydrolase obtained by the above methods.

TABLE 5

Purification of creatine amidinohydrolase from Escherichia Coli JM109 (pCRH273M3)

| Step | Total activity (U) | Specific activity (U/mg-protein) | Yield (%) |
|---|---|---|---|
| French press rupture | 49800 | | 100.0 |
| $(NH_4)_2SO_4$ precipitation-redissolution | 43027 | 8.3 | 86.4 |
| Sephadex G-25 | 39989 | 9.9 | 80.3 |
| Octyl Sepharose CL-6B | 32021 | 14.8 | 64.3 |

TABLE 6

Physicochemical properties of creatine amidinohydrolase purified from Escherichia coli JM109 (pCRH273M3)

| Item | Physicochemical properties |
|---|---|
| Action | creatine + $H_2O$ → sarcosine + urea |
| Optimal temperature | ca. 40° C.–45° C. |
| Optimal pH | ca. 8.0–9.0 |
| Thermal stability | ca. 40° C. (50 mM potassium phosphate buffer, pH 7.5, 30 min treatment) |
| pH stability | ca. 5–8 (40° C., 18 hr preservation) |
| Km value | ca. 9.0 mM (creatine) |
| Molecular weight | ca. 43,000 (SDS-PAGE) |
| Isoelectric point | ca. [3.5] *4.5* (isoelectric focusing) |

The following Table 7 summarizes the Km values for creatine of the novel creatine amidinohydrolases of the present invention and wild creatine amidinohydrolase. As is evident from Table 7, the novel creatine amidinohydrolases of the present invention had reduced Km value as compared to the wild creatine amidinohydrolase.

TABLE 7

| Enzyme | Km value |
|---|---|
| wild | 15.2 mM |
| pCRH273M1 | 6.5 mM |
| pCRH273M2 | 4.5 mM |
| pCRH273M3 | 9.0 mM |

Example 7

Using the purified creatine amidinohydrolase prepared in Example 5 and wild creatine amidinohydrolase, a creatinine determination reagent having the following composition was prepared, and the amounts of the creatine amidinohydrolase necessary for giving a creatinine determination reagent was compared.

| | |
|---|---|
| creatine amidinohydrolase of Example 5 or wild creatine amidinohydrolase | 20, 40, 60 U/ml |
| creatinine amidohydrolase | 150 U/ml |
| sarcosine oxidase | 7 U/ml |
| peroxidase | 3 PU/ml |
| MOPS buffer | 0.1 M, pH 8.0 |
| Triton X-100 | 0.1% |
| 4-aminoantipyrine | 0.15 mM |
| TOOS (aniline derivative) | 0.2 mM |

The above-mentioned solution (3 ml) was added to a sample (60 $\mu$l) containing creatinine (100 mg/dl) and changes in absorbance were determined at 37° C. at wavelength 546 nm. The time course results are shown in FIG. 2.

In the Figure, "Wild" shows a wild certainty amidinohydrolase and "pCRH273M2" is the creatine amidinohydrolase of the present invention.

Figure 2:
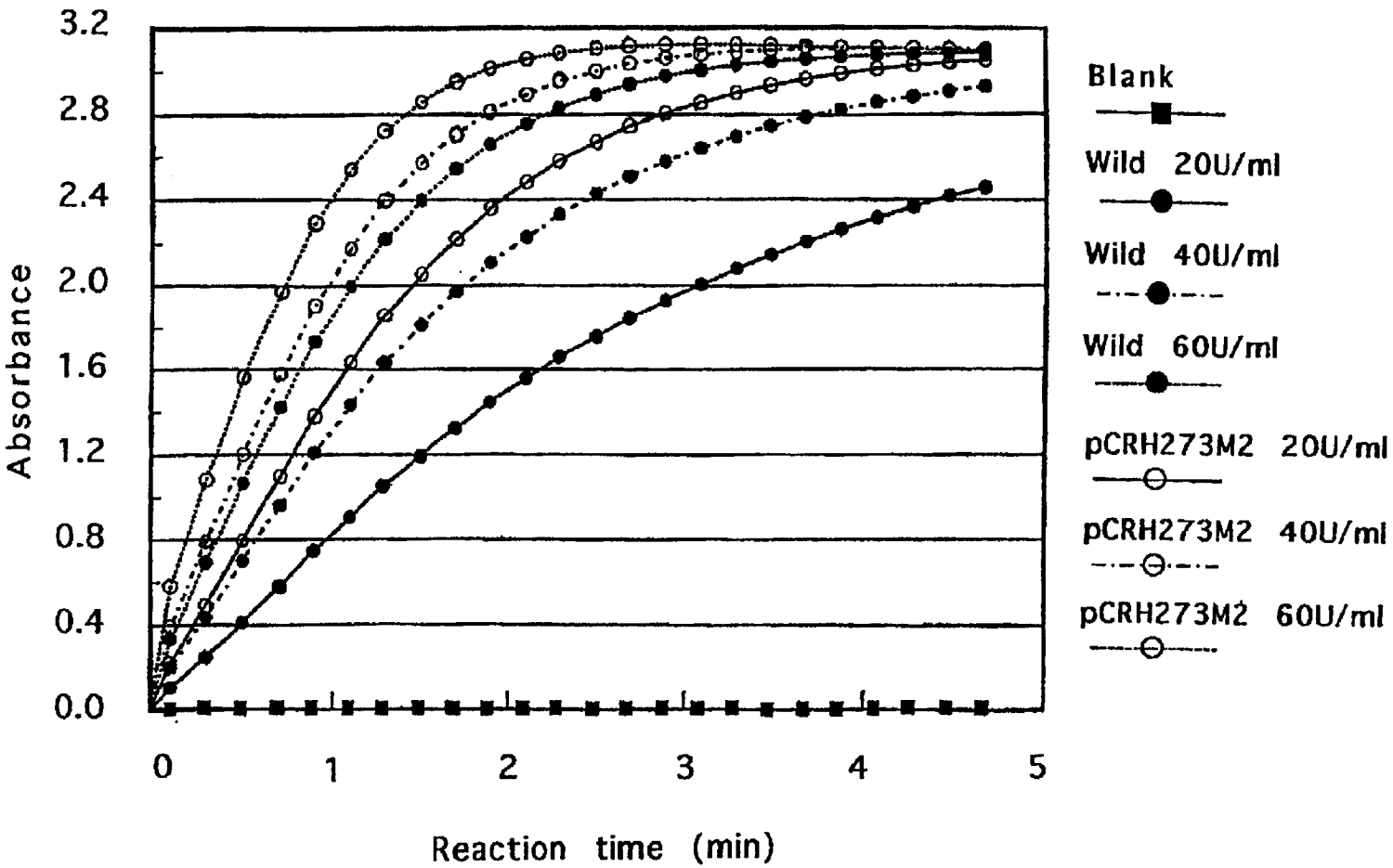
FIG. 2 shows the time course determination results of creatinine in a sample, by the use of the creatine amidinohydrolase of the present invention and a wild creatine amidinohydrolase.

As is evident from FIG. 2, when the determination was ended in 5 minutes, the creatine amidinohydrolase of the present invention enabled determination with less enzyme amount (ca. ⅓ amount) as compared to the wild creatine amidinohydrolase. It was also confirmed that the reactivity during the latter half of the determination, i.e., when the creatine in the sample decreased, was fine.

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
(A) LENGTH: 404 amino acids
(B) TYPE: amino acid
(D) TOPOLOGY: linear (ii) MOLECULE TYPE: <Unknown>
(A) DESCRIPTION: protein (vi) ORIGINAL SOURCE:
(A) ORGANISM: Alcaligenes faecalis
(B) STRAIN: TE3581 (FERM P-14237)

(ix) FEATURE:
(A) NAME/KEY: mat peptide
(B) LOCATION: 1 to 404
(D) OTHER INFORMATION: protein having creatine amidinohydrolase activity (xi) SEQUENCE DESCRIPTION: SEQ ID NO: 1:

```
Met Thr Asp Asp Met Leu His Val Met Lys Trp His Asn Gly Glu Lys
  1               5                  10                  15

Asp Tyr Ser Pro Phe Ser Asp Ala Glu Met Thr Arg Arg Gln Asn Asp
             20                  25                  30

Val Arg Gly Trp Met Ala Lys Asn Asn Val Asp Ala Ala Leu Phe Thr
         35                  40                  45

Ser Tyr His Cys Ile Asn Tyr Tyr Ser Gly Trp Leu Tyr Cys Tyr Phe
     50                  55                  60

Gly Arg Lys Tyr Gly Met Val Ile Asp His Asn Asn Ala Thr Thr Ile
 65                  70                  75                  80

Ser Ala Gly Ile Asp Gly Gly Gln Pro Trp Arg Arg Ser Phe Gly Asp
                 85                  90                  95

Asn Ile Thr Tyr Thr Asp Trp Arg Arg Asp Asn Phe Tyr Arg Ala Val
            100                 105                 110

Arg Gln Leu Thr Thr Gly Ala Lys Arg Ile Gly Ile Glu Phe Asp His
        115                 120                 125

Val Asn Leu Asp Phe Arg Arg Gln Leu Glu Glu Ala Leu Pro Gly Val
    130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Cys Asp
                165                 170                 175

Val Gly Gly Ala Ala Cys Ala Ala Ala Ile Lys Ala Gly Val Pro Glu
            180                 185                 190

His Glu Val Ala Ile Ala Thr Thr Asn Ala Met Ile Arg Glu Ile Ala
        195                 200                 205

Lys Ser Phe Pro Phe Val Glu Leu Met Asp Thr Trp Thr Trp Phe Gln
    210                 215                 220
```

-continued

```
Ser Gly Ile Asn Thr Asp Gly Ala His Asn Pro Val Thr Asn Arg Ile
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
        275                 280                 285

Gly Leu Glu Leu Ile Lys Pro Gly Ala Arg Cys Lys Asp Ile Ala Ile
    290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Asp Thr Glu Leu Lys Pro
            340                 345                 350

Gly Met Val Val Ser Met Glu Pro Met Val Met Leu Pro Glu Gly Met
        355                 360                 365

Pro Gly Ala Gly Gly Tyr Arg Glu His Asp Ile Leu Ile Val Gly Glu
    370                 375                 380

Asp Gly Ala Glu Asn Ile Thr Gly Phe Pro Phe Gly Pro Glu His Asn
385                 390                 395                 400

Ile Ile Arg Asn
            404
```

(2) INFORMATION FOR SEQ ID NO: 2:

(i) SEQUENCE CHARACTERISTICS:
(A) LENGTH: 1212 base pairs
(B) TYPE: nucleic acid
(C) STRANDEDNESS: double
(D) TOPOLOGY: linear (ii) MOLECULE TYPE: genomic DNA (vi) ORIGINAL SOURCE:
(A) ORGANISM: Alcaligenes faecalis
(B) STRAIN: TE3581 (FERM P-14237)

(ix) FEATURE:
(A) NAME/KEY: CDS
(B) LOCATION: 1 to 1212

(xi) SEQUENCE DESCRIPTION: SEQ ID NO: 2:

```
ATG ACT GAC GAC ATG TTG CAC GTG ATG AAA TGG CAC AAC GGC GAG AAA      48
Met Thr Asp Asp Met Leu His Val Met Lys Trp His Asn Gly Glu Lys
  1               5                  10                  15

GAT TAT TCG CCG TTT TCG GAT GCC GAG ATG ACC CGC CGC CAA AAC GAC      96
Asp Tyr Ser Pro Phe Ser Asp Ala Glu Met Thr Arg Arg Gln Asn Asp
             20                  25                  30

GTT CGC GGC TGG ATG GCC AAG AAC AAT GTC GAT GCG GCG CTG TTC ACC     144
Val Arg Gly Trp Met Ala Lys Asn Asn Val Asp Ala Ala Leu Phe Thr
         35                  40                  45

TCT TAT CAC TGC ATC AAC TAC TAT TCC GGC TGG CTG TAC TGC TAT TTC     192
Ser Tyr His Cys Ile Asn Tyr Tyr Ser Gly Trp Leu Tyr Cys Tyr Phe
     50                  55                  60

GGA CGC AAG TAC GGC ATG GTC ATC GAC CAC AAC AAC GCC ACG ACG ATT     240
Gly Arg Lys Tyr Gly Met Val Ile Asp His Asn Asn Ala Thr Thr Ile
 65                  70                  75                  80

TCG GCC GGC ATC GAC GGC GGC CAG CCC TGG CGC CGC AGC TTC GGC GAC     288
```

-continued

```
Ser Ala Gly Ile Asp Gly Gly Gln Pro Trp Arg Arg Ser Phe Gly Asp
                85                  90                  95

AAC ATC ACC TAC ACC GAC TGG CGC CGC GAC AAT TTC TAT CGC GCC GTG      336
Asn Ile Thr Tyr Thr Asp Trp Arg Arg Asp Asn Phe Tyr Arg Ala Val
            100                 105                 110

CGC CAG CTG ACC ACG GGC GCC AAG CGC ATC GGC ATC GAG TTC GAC CAC      384
Arg Gln Leu Thr Thr Gly Ala Lys Arg Ile Gly Ile Glu Phe Asp His
        115                 120                 125

GTC AAT CTC GAC TTC CGC CGC CAG CTC GAG GAA GCC CTA CCG GGC GTC      432
Val Asn Leu Asp Phe Arg Arg Gln Leu Glu Glu Ala Leu Pro Gly Val
    130                 135                 140

GAC TTC GTC GAC ATC AGC CAG CCC TCG ATG TGG ATG CGC ACC ATC AAG      480
Glu Phe Val Asp Ile Ser Gln Pro Ser Met Trp Met Arg Thr Ile Lys
145                 150                 155                 160

TCG CTC GAA GAG CAG AAG CTG ATC CGC GAA GGC GCC CGC GTG TGT GAC      528
Ser Leu Glu Glu Gln Lys Leu Ile Arg Glu Gly Ala Arg Val Cys Asp
                165                 170                 175

GTC GGC GGC GCG GCC TGC GCG GCT GCC ATC AAG GCC GGC GTG CCC GAG      576
Val Gly Gly Ala Ala Cys Ala Ala Ala Ile Lys Ala Gly Val Pro Glu
            180                 185                 190

CAT GAA GTG GCG ATC GCC ACC ACC AAT GCG ATG ATC CGC GAG ATC GCC      624
His Glu Val Ala Ile Ala Thr Thr Asn Ala Met Ile Arg Glu Ile Ala
        195                 200                 205

AAA TCG TTC CCC TTC GTG GAG CTG ATG GAC ACC TGG ACC TGG TTC CAG      672
Lys Ser Phe Pro Phe Val Glu Leu Met Asp Thr Trp Thr Trp Phe Gln
    210                 215                 220

TCG GGC ATC AAC ACC GAC GGC GCG CAC AAT CCG GTC ACC AAC CGC ATC      720
Ser Gly Ile Asn Thr Asp Gly Ala His Asn Pro Val Thr Asn Arg Ile
225                 230                 235                 240

GTG CAA TCC GGC GAC ATC CTT TCG CTC AAC ACC TTC CCG ATG ATC TTC      768
Val Gln Ser Gly Asp Ile Leu Ser Leu Asn Thr Phe Pro Met Ile Phe
                245                 250                 255

GGC TAC TAC ACC GCG CTG GAG CGC ACG CTG TTC TGC GAC CAT GTC GAT      816
Gly Tyr Tyr Thr Ala Leu Glu Arg Thr Leu Phe Cys Asp His Val Asp
            260                 265                 270

GAC GCC AGC CTC GAC ATC TGG GAG AAG AAC GTG GCC GTG CAT CGC CGC      864
Asp Ala Ser Leu Asp Ile Trp Glu Lys Asn Val Ala Val His Arg Arg
        275                 280                 285

GGG CTC GAG CTG ATC AAG CCG GGC GCG CGC TGC AAG GAC ATC GCC ATC      912
Gly Leu Glu Leu Ile Lys Pro Gly Ala Arg Cys Lys Asp Ile Ala Ile
    290                 295                 300

GAG CTC AAC GAG ATG TAC CGC GAG TGG GAC CTG CTG AAG TAC CGC TCC      960
Glu Leu Asn Glu Met Tyr Arg Glu Trp Asp Leu Leu Lys Tyr Arg Ser
305                 310                 315                 320

TTC GGC TAT GGC CAC TCC TTC GGC GTG CTG TGC CAC TAC TAC GGT CGC     1008
Phe Gly Tyr Gly His Ser Phe Gly Val Leu Cys His Tyr Tyr Gly Arg
                325                 330                 335

GAG GCC GGC GTG GAG CTG CGC GAG GAC ATC GAC ACC GAG CTG AAG CCC     1056
Glu Ala Gly Val Glu Leu Arg Glu Asp Ile Asp Thr Glu Leu Lys Pro
            340                 345                 350

GGC ATG GTG GTC TCC ATG GAG CCG ATG GTG ATG CTG CCG GAG GGC ATG     1104
Gly Met Val Val Ser Met Glu Pro Met Val Met Leu Pro Glu Gly Met
        355                 360                 365

CCC GGT GCC GGC GGC TAT CGC GAG CAC GAC ATC CTG ATC GTC GGG GAG     1152
Pro Gly Ala Gly Gly Tyr Arg Glu His Asp Ile Leu Ile Val Gly Glu
    370                 375                 380

GAC GGT GCC GAG AAC ATC ACC GGC TTC CCG TTC GGT CCG GAA CAC AAC     1200
Asp Gly Ala Glu Asn Ile Thr Gly Phe Pro Phe Gly Pro Glu His Asn
385                 390                 395                 400
```

-continued

```
ATC ATC CGC AAC                                                    1212
Ile Ile Arg Asn
            404


(2) INFORMATION FOR SEQ ID NO: 3:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: other nucleic acid (synthetic DNA)

    (xi) SEQUENCE DESCRIPTION: SEQ ID NO: 3:

CAACATGTCG TCAGTCATAT GTGTTTCCTG TGTGAAATT                          39
```

What is claimed is:

[1. A creatine amidinohydrolase having the following physicochemical properties:

Action: catalyzing the following reaction;

creatine+$H_2O$→sarcosine+urea

Optimum temperature: about 40–50° C.

Optimum pH: pH about 8.0–9.0

$K_m$ value for creatine in a coupling assay using a sarcosine oxidase and a peroxidase: 3.5–10.0 mM Molecular weight: about 43,000 (SDS-PAGE)

Isoelectric point: about 3.5.]

[2. A creatine amidinohydrolase having the following physicochemical properties:

Action: catalyzing the following reaction;

creatine+$H_2O$→sarcosine+urea

Optimum temperature: about 40–50° C.

Optimum pH: about 8.0–9.0

$K_m$ value for creatine in a coupling assay using a sarcosine oxidase and a peroxidase: 4.5±1.0 mM Molecular weight: about 43,000 (SDS-PAGE)

Isoelectric point: about 3.5.]

[3. The creatine amidinohydrolase of claim 2, which is obtained from Escherichia coli JM109 (pCRH273M2) (FERM BP-5375).]

[4. A creatine amidinohydrolase having the following physiocochemical properties:

Action: catalyzing the following reaction;

creatine+$H_2O$→sarcosine+urea

Optimum temperature: about 40–50° C.

Optimum pH: pH about 8.0–9.0

$K_m$ value for creatine in a coupling assay using a sarcosine oxidase and a peroxidase: 6.5±1.0 mM Molecular weight: about 43,000 (SDS-PAGE)

Isoelectric point: about 3.5.]

[5. The creatine amidinohydrolase of claim 4, which is obtained from Escherichia coli JM109 (pCRH273M1) (FERM BP-5374).]

[6. A creatine amidinohydrolase having the following physicochemical properties:

Action: catalyzing the following reaction;

creatine+$H_2O$→sarcosine+urea

Optimum temperature: about 40–50° C.

Optimum pH: pH about 8.0–9.0

$K_m$ value for creatine in a coupling assay using a sarcosine oxidase and a peroxidase: 9.0±1.0 mM Molecular weight: about 43,000 (SDS-PAGE)

Isoelectric point: about 3.5.]

[7. The creatine amidinohydrolase of claim 6, which is obtained from Escherichia coli JM109 (pCRH273M3) (FERM BP-5376).]

[8. A method for producing the creatine amidinohydrolase of claim 1, comprising culturing a microorganism producing said creatine amidinohydrolase in a nutrient medium and recovering said creatine amidinohydrolase from the resulting culture.]

[9. The method of claim 8, wherein said microorganism is selected from the group consisting of Escherichia coli JM109 (pCRH273M1) (FERM BP-5374), Escherichia coli JM109 (pCRH273M2) (FERM BP-5375), and Escherichia coli JM109 (pCRH273M3) (FERM BP-5376).]

[10. A reagent for determination of creatine in a sample, comprising the creatine amidinohydrolase of claim 1, a sarcosine oxidase, and a composition for the detection of hydrogen peroxide.]

[11. The reagent of claim 10, in which the composition for the detection of hydrogen peroxide comprises an enzyme having a peroxidase activity, a chromophore, and a buffer.]

[12. The reagent of claim 11, in which the enzyme having the peroxidase activity is selected from the group consisting of peroxidase, haloperoxidase, bromoperoxidase, lactoperoxidase, and myeloperoxidase.]

[13. The reagent of claim 11, in which the chromophore comprises a hydrogen receptor and a coupler.]

[14. The reagent of claim 13, in which the hydrogen receptor is 4-aminoantipyrine or a 3-methyl-2-benzothiazoline-hydrazine derivative.]

[15. The reagent of claim 13, in which the coupler is an aniline derivative or a phenol derivative.]

[16. A method for determining creatine in a sample, which comprises measuring absorbance of the pigment produced by the reaction of the reagent of claim 10 with the sample.]

[17. A reagent for determination of creatinine in sample, comprising a creatinine amidohydrolase, the creatine amidinohydrolase of claim 1, a sarcosine oxidase, and a composition for the detection of hydrogen peroxide.]

[18. The reagent of claim 17, in which the composition for the detection of hydrogen peroxide comprises and enzyme having a peroxidase activity, a chromophore, and a buffer.]

[19. The reagent of claim 18, in which the enzyme having the peroxidase activity is selected from the group consisting of peroxidase, haloperoxidase, bromoperoxidase, lactoperoxidase and myeloperoxidase.]

[20. The reagent of claim 18, in which the chromophore comprises a hydrogen receptor and a coupler.]

[21. The reagent of claim 20, in which the hydrogen receptor is 4-aminoantipyrine or a 3-methyl-2-benzothiazoline-hydrozine derivative.]

[22. The reagent of claim 20, in which the coupler is an aniline derivative or a phenol derivative.]

[23. A method for determining creatinine in a sample, which comprises measuring absorbance of the pigment produced by the reaction of the reagent of claim 17 with the sample.]

*24. A creatine amidinohydrolase (i) encoded by a nucleic acid sequence obtained by mutating (a) the nucleic acid sequence of SEQ ID NO:2 or (b) a nucleic acid sequence encoding the amino acid sequence of SEQ ID NO:1 and (ii) having the following physicochemical properties:*

*Action: catalyzing the following reaction: creatine+$H_2O$→sarcosine+urea*

*Km values for creatine in a coupling assay using a sarcosine oxidase and a peroxidase: 3.5–10.0 mM*

*Optimum temperature: about 40–50° C. (at pH of about 7.5)*

*Optimum pH: pH about 8.0–9.0 (at a temperature of about 37° C.)*

*Molecular weight: about 43,000 (SDS-PAGE)*

*Isoelectric point of 4.5.*

*25. A creatine amidinohydrolase (i) encoded by a nucleic acid sequence obtained by mutating (a) the nucleic acid sequence of SEQ ID NO:2 or (b) a nucleic acid sequence encoding the amino acid sequence of SEQ ID NO:1 and (ii) having the following physicochemical properties:*

*Action: catalyzing the following reaction: creatine+$H_2O$→sarcosine+urea*

*Km values for creatine in a coupling assay using a sarcosine oxidase and a peroxidase: 4.5±1.0 mM*

*Optimum temperature: about 40–50° C. (at pH of about 7.5)*

*Optimum pH: pH about 8.0–9.0 (at a temperature of about 37° C.)*

*Molecular weight: about 43,000 (SDS-PAGE)*

*Isoelectric point: about 4.5.*

*26. A creatine amidinohydrolase (i) encoded by a nucleic acid sequence obtained by mutating (a) the nucleic acid sequence of SEQ ID NO:2 or (b) a nucleic acid sequence encoding the amino acid sequence of SEQ ID NO:1 and (ii) having a following physicochemical properties:*

*Action: catalyzing the following reaction: creatine+$H_2O$→sarcosine+urea*

*Km values for creatine in a coupling assay using a sarcosine oxidase and a peroxidase: 6.5±1.0 mM*

*Optimum temperature: about 40–50° C. (at pH of about 7.5)*

*Optimum pH: pH about 8.0–9.0 (at a temperature of about 37° C.)*

*Molecular weight: about 43,000 (SDS-PAGE)*

*Isoelectric point: about 4.5.*

*27. A creatine amidinohydrolase (i) encoded by a nucleic acid sequence obtained by mutating (a) the nucleic acid sequence of SEQ ID NO:2 or (b) a nucleic acid sequence encoding the amino acid sequence of SEQ ID NO:1 and (ii) having the following physiocochemical properties:*

*Action: catalyzing the following reaction: creatine+$H_2O$→sarcosine+urea*

*Km values for creatine in a coupling assay using a sarcosine oxidase and a peroxidase: 9.0±1.0 mM*

*Optimum temperature: about 40–50° C. (at pH of about 7.5)*

*Optimum pH: about 8.0–9.0 (at a temperature of about 37° C.)*

*Molecular weight: about 43,000 (SDS-PAGE)*

*Isoelectric point: about 4.5.*

*28. A method for producing the creatine amidinohydrolase of claim 24, comprising culturing a microorganism producing said creatine amidinohydrolase in a nutrient medium and recovering said creatine amidinohydrolase from the resulting culture.*

*29. A reagent for determination of creatine in a sample, comprising the creatine amidinohydrolase of claim 24, a sarcosine oxidase, and a composition for the detection of hydrogen peroxide.*

*30. A method for determining a creatine in a sample, which comprises measuring absorbance of a pigment produced by the reaction of the reagent of claim 29 with the sample.*

*31. A reagent for determination of creatinine in a sample, comprising a creatinine amidohydrolase, the creatine amidinohydrolase of claim 24, a sarcosine oxidase, and a composition for the detection of hydrogen peroxide.*

*32. A method for determining creatinine in a sample, which comprises measuring-absorbance of a pigment produced by the reaction of the reagent of claim 31 with the sample.*

*33. A method for producing the creatine amidinohydrolase of claim 25, comprising culturing a microorganism producing said creatine amidinohydrolase in a nutrient medium and recovering said creatine amidinohydrolase from the resulting culture.*

*34. A reagent for determination of creatine in a sample, comprising the creatine amidinohydrolase of claim 25, a sarcosine oxidase, and a composition for the detection of hydrogen peroxide.*

*35. A method for determining creatine in a sample, which comprises measuring-absorbance of a pigment produced by the reaction of the reagent of claim 34 with the sample.*

*36. A reagent for determination of creatinine in a sample, comprising a creatinine amidohydrolase, the creatine amidinohydrolase of claim 25, a sarcosine oxidase, and a composition for the detection of hydrogen peroxide.*

*37. A method for determining creatinine in a sample, which comprises measuring-absorbance of a pigment produced by the reaction of the reagent of claim 36 with the sample.*

*38. A creatine amidinohydrolase having the following physicochemical properties:*

*Action: catalyzing the following reaction; creatine+$H_2O$→sarcosine+urea*

*Optimum temperature: about 40–50° C.(at pH of about 7.5)*

*Optimum pH: pH about 8.0–9.0 (at a temperature of about 37° C.)*

*$K_m$ value for creatine in a coupling assay using a sarcosine oxidase and a peroxidase: 3.5–10.0 mM*

*Molecular weight: about 43,000 (SDS-PAGE)*

*Isoelectric point: about 4.5.*

*39. A creatine amidinohydrolase having the following physicochemical properties:*

*Action: catalyzing the following reaction; creatine+$H_2O$→sarcosine+urea*

*Optimum temperature: about 40–50° C. (at pH of about 7.5)*

*Optimum pH: about 8.0–9.0 (at temperature of about 37° C.)*

*$K_m$ value for creatine in a coupling assay using a sarcosine oxidase and a peroxidase: 4.5±1.0 mM*

*Molecular weight: about 43,000 (SDS-PAGE)*

*Isoelectric point: about 4.5.*

*40. The creatine amidinohydrolase of claim 39, which is obtained from Escherichia coli JM109 (pCRH273M2) (FERM BP-5375).*

*41. A creatine amidinohydrolase having the following physiocochemical properties:*

*Action: catalyzing the following reaction; creatine+$H_2O$→sarcosine+urea*

*Optimum temperature: about 40–50° C. (at pH of about 7.5)*

*Optimum pH: pH about 8.0–9.0 (at a temperature of about 37° C.)*

*$K_m$ value for creatine in a coupling assay using a sarcosine oxidase and a peroxidase: 6.5±1.0 mM*

*Molecular weight: about 43,000 (SDS-PAGE)*

*Isoelectric point: about 4.5.*

*42. The creatine amidinohydrolase of claim 41, which is obtained from Escherichia coli JM109 (pCRH273M1) (FERM BP-5374).*

*43. A creatine amidinohydrolase having the following physicochemical properties:*

*Action: catalyzing the following reaction; creatine+$H_2O$→sarcosine+urea*

*Optimum temperature: about 40–50° C. (at pH of about 7.5)*

*Optimum pH: pH about 8.0–9.0 (at a temperature of about 37° C.)*

*$K_m$ value for creatine in a coupling assay using a sarcosine oxidase and a peroxidase: 9.0±1.0 mM*

*Molecular weight: about 43,000 (SDS-PAGE)*

*Isoelectric point: about 4.5.*

*44. The creatine amidinohydrolase of claim 43, which is obtained from Escherichia coli JM109 (pCRH273M3) (FERM BP-5376).*

*45. A method for producing the creatine amidinohydrolase of claim 38, comprising culturing a microorganism producing said creatine amidinohydrolase in a nutrient medium and recovering said creatine amidinohydrolase from the resulting culture.*

*46. The method of claim 45, wherein said microorganism is selected from the group consisting of Escherichia coli JM109 (pCRH273M1)(FERM BP-5374), Escherichia coli JM109 (pCRH273M2)(FERM BP-5375), and Escherichia coli JM109 (pCRH273M3)(FERM BP-5376).*

*47. A reagent for determination of creatine in a sample, comprising the creatine amidinohydrolase of claim 38, a sarcosine oxidase, and a composition for the detection of hydrogen peroxide.*

*48. The reagent of claim 47, in which the composition for the detection of hydrogen peroxide comprises an enzyme having a peroxidase activity, a chromophore, and a buffer.*

*49. The reagent of claim 48, in which the enzyme having the peroxidase activity is selected from the group consisting of peroxidase, haloperoxidase, bromoperoxidase, lactoperoxidase, and myeloperoxidase.*

*50. The reagent of claim 48, in which the chromophore comprises a hydrogen receptor and a coupler.*

*51. The reagent of claim 50, in which the hydrogen receptor is 4-aminoantipyrine or a 3-methyl-2-benzothiazoline-hydrazine derivative.*

*52. The reagent of claim 50, in which the coupler is an aniline derivative or a phenol derivative.*

*53. A method for determining creatine in a sample, which comprises measuring absorbance of the pigment produced by the reaction of the reagent of claim 47 with the sample.*

*54. A reagent for determination of creatinine in sample, comprising a creatinine amidohydrolase, the creatine amidinohydrolase of claim 15, a sarcosine oxidase, and a composition for the detection of hydrogen peroxide.*

*55. The reagent of claim 54, in which the composition for the detection of hydrogen peroxide comprises and enzyme having a peroxidase activity, a chromophore, and a buffer.*

*56. The reagent of claim 55, in which the enzyme having the peroxidase activity is selected from the group consisting of peroxidase, haloperoxidase, bromoperoxidase, lactoperoxidase, and myeloperoxidase.*

*57. The reagent of claim 55, in which the chromophore comprises a hydrogen receptor and a coupler.*

*58. The reagent of claim 57, in which the hydrogen receptor is 4-aminoantipyrine or a 3-methyl-2-benzothiazoline-hydrozine derivative.*

*59. The reagent of claim 57, in which the coupler is an aniline derivative or a phenol derivative.*

*60. A method for determining creatinine in a sample, which comprises measuring absorbance of the pigment produced by the reaction of the reagent of claim 54 with the sample.*

* * * * *

UNITED STATES PATENT AND TRADEMARK OFFICE

CERTIFICATE OF CORRECTION

PATENT NO. : RE 38,687 E
DATED : January 11, 2005
INVENTOR(S) : Sogabe et al.

It is certified that error appears in the above-identified patent and that said Letters Patent is hereby corrected as shown below:

Title page,
Item [57], ABSTRACT,
Line 3, “following reaction;” should read -- following reaction: --.
Line 11, “Molecule weight” should read -- Molecular weight --.

Column 1,
Line 32, “chronic neophritis, acute neophritis” should read -- chronic nephritis, acute nephritis --.

Column 2,
Line 3, “genus, Alcaligenes” should read -- genus Alcaligenes --.
Line 15, “cell lines” should read -- cell line --.
Line 34, “creatine and” should read -- creatine --.

Column 4,
Line 43, “incubated” should read -- inoculated --.
Line 54, “obtain” should read -- obtained --.

Column 5,
Line 6, “microorganisms” should read -- microorganism --.

Column 6,
Line 11, “on a rate method” should read -- or a rate method --.
Line 27, “detecting the creatine” should read -- detecting creatine --.
Line 37, “peroxide activity” should read -- peroxidase activity --.
Line 40, “lactoperoxidase” should read -- ,lactoperoxidase --.
Line 45, “hydrozine” should read -- hydrazine --.

Column 7,
Line 19, “0.3 H” should read -- 0.3 M --.
Line 23, “sarcosine cridase” should read -- sarcosine oxidase --.
Line 42, “dilutions fold” should read -- dilution fold --.

Column 8,
Line 17, “creatinine” should read -- creatine --.
Line 20, “restriction enzymes” should read -- restriction enzyme --.
Line 42, “obtained in” should read -- cultured in --.

UNITED STATES PATENT AND TRADEMARK OFFICE

CERTIFICATE OF CORRECTION

PATENT NO. : RE 38,687 E
DATED : January 11, 2005
INVENTOR(S) : Sogabe et al.

It is certified that error appears in the above-identified patent and that said Letters Patent is hereby corrected as shown below:

Column 9,
Line 26, “record” should read -- reduced --.
Line 39, “the ration of two kinds” should read -- the ratio of the two kinds --.
Line 40, “concentration + activity” should read -- concentration ÷ activity --.
Line 44, “20,00” should read -- 20,000 --.
Line 58, “filtration were” should read -- filtration, were --.

Column 10,
Line 55, “or creatine amidinohydrolase” should read -- of creatine amidinohydrolase --.

Column 12,
Line 34, “Km value” should read -- Km values --.

Column 13,
Line 1, “wild certainty” should read -- wild creatine --.

Column 21,
Line 47, “having a following” should read -- having the following --.

Column 22,
Lines 25, 38 and 45, “measuring-absorbance” should read -- measuring absorbance --.

Column 23,
Line 1, “at temperature” should read -- at a temperature --.

Column 24,
Line 26, “in sample” should read -- in a sample --.
Line 28, “claim 15” should read -- claim 38 --.
Line 31, “and enzyme” should read -- an enzyme --.

UNITED STATES PATENT AND TRADEMARK OFFICE

CERTIFICATE OF CORRECTION

PATENT NO. : RE 38,687 E
DATED : January 11, 2005
INVENTOR(S) : Sogabe et al.

It is certified that error appears in the above-identified patent and that said Letters Patent is hereby corrected as shown below:

Column 24 (cont'd),
Line 41, "hydrozine" should read -- hydrazine --.

Signed and Sealed this

Twenty-eighth Day of February, 2006

JON W. DUDAS
*Director of the United States Patent and Trademark Office*